United States Patent
Heerink et al.

(10) Patent No.: US 12,161,325 B2
(45) Date of Patent: Dec. 10, 2024

(54) SURGICAL FORCEPS AND STAPLER

(71) Applicant: Stichting Het Nederlands Kanker Instituut—Antoni van Leeuwenhoek Ziekenhuis, Amsterdam (NL)

(72) Inventors: Wouter Johannes Heerink, Amsterdam (NL); Harald Christian Groen, Amsterdam (NL); Theodoor Jacques Marie Ruers, Amsterdam (NL)

(73) Assignee: Stichting Het Nederlands Kanker Instituut—Antoni van Leeuwenhoek Ziekenhuis, Amsterdam (NL)

( * ) Notice: Subject to any disclaimer, the term of this patent is extended or adjusted under 35 U.S.C. 154(b) by 0 days.

(21) Appl. No.: 18/040,270

(22) PCT Filed: Aug. 4, 2021

(86) PCT No.: PCT/NL2021/050492
§ 371 (c)(1),
(2) Date: Feb. 2, 2023

(87) PCT Pub. No.: WO2022/031169
PCT Pub. Date: Feb. 10, 2022

(65) Prior Publication Data
US 2023/0355234 A1 Nov. 9, 2023

(30) Foreign Application Priority Data
Aug. 4, 2020 (NL) .................................... 2026208

(51) Int. Cl.
*A61B 17/072* (2006.01)
*A61B 17/068* (2006.01)
(Continued)

(52) U.S. Cl.
CPC ...... *A61B 17/072* (2013.01); *A61B 17/07207* (2013.01); *A61B 17/068* (2013.01);
(Continued)

(58) Field of Classification Search
CPC ............... A61B 17/068; A61B 17/072; A61B 17/07207; A61B 17/07292; A61B 17/29;
(Continued)

(56) References Cited

U.S. PATENT DOCUMENTS 8,512,318 B2 * 8/2013 Tovey ............... A61B 34/70
606/1
9,603,512 B2 * 3/2017 Hoeg ............. A61B 1/00016
(Continued)

FOREIGN PATENT DOCUMENTS

EP 1943976 A2 7/2008
EP 3226794 A1 10/2017
(Continued)

*Primary Examiner* — Scott A Smith
(74) *Attorney, Agent, or Firm* — N.V. Nederlandsch Octrooibureau

(57) ABSTRACT

A surgical forceps comprises a first jaw (101) and a second jaw (102), the first jaw (101) and the second jaw (102) being configured to be rotated relative to each other around an axis of rotation (104). A position sensor (105) is capable of sensing a first orientation with respect to a first axis (106) and a second orientation with respect to a second axis (107) different from the first axis (106), wherein the first axis (106)
(Continued)

and the second axis (107) are orthogonal to the axis of rotation (104). The surgical forceps comprises a stapler (108) for stapling a tissue grasped by the surgical forceps (100) and a cutter (103) for cutting the tissue grasped by the surgical forceps (100) along a line.

13 Claims, 6 Drawing Sheets

(51) Int. Cl.
*A61B 17/295* (2006.01)
*A61B 18/14* (2006.01)
*A61B 34/00* (2016.01)
*A61B 34/20* (2016.01)

(52) U.S. Cl.
CPC ............... *A61B 2017/07214* (2013.01); *A61B 2017/07271* (2013.01); *A61B 2017/07285* (2013.01); *A61B 17/295* (2013.01); *A61B 18/1442* (2013.01); *A61B 34/20* (2016.02); *A61B 34/76* (2016.02)

(58) Field of Classification Search
CPC . A61B 17/295; A61B 17/32; A61B 17/00234; A61B 17/115; A61B 2017/07214; A61B 2017/07271; A61B 2017/07285; A61B 34/20; A61B 34/30; A61B 34/76; A61B 18/1442; A61B 18/1447

USPC .............. 227/19, 175.1, 176.1, 175.2, 180.1; 606/1, 139, 219

See application file for complete search history.

(56) References Cited

U.S. PATENT DOCUMENTS

| | | | |
|---|---|---|---|
| 9,943,377 B2* | 4/2018 | Yates | A61B 17/295 |
| 10,582,832 B2* | 3/2020 | Lawrence | A61B 1/00101 |
| 10,702,349 B2* | 7/2020 | Overmyer | A61B 17/07207 |
| 10,987,121 B2* | 4/2021 | Gladstone | A61B 17/1622 |
| 11,311,347 B2* | 4/2022 | Hingwe | A61B 34/35 |
| 11,523,839 B2* | 12/2022 | Wellman | A61B 17/29 |
| 2008/0211634 A1* | 9/2008 | Hopkins | H04N 23/54 |
| | | | 348/E5.043 |
| 2009/0099544 A1 | 4/2009 | Munrow et al. | |
| 2011/0119224 A1* | 5/2011 | Mangione-Smith | G16H 50/50 |
| | | | 340/407.1 |
| 2011/0282360 A1* | 11/2011 | Tovey | A61B 34/30 |
| | | | 606/130 |
| 2018/0000543 A1* | 1/2018 | Hibner | A61B 34/20 |
| 2018/0116731 A1 | 5/2018 | State et al. | |
| 2019/0254762 A1 | 8/2019 | Overmyer | |

FOREIGN PATENT DOCUMENTS

| | | |
|---|---|---|
| WO | 97/03609 A1 | 2/1997 |
| WO | 2015/035178 A2 | 3/2015 |
| WO | 2017/054817 A1 | 4/2017 |
| WO | 2019/147129 A2 | 8/2019 |

\* cited by examiner

SURGICAL FORCEPS AND STAPLER

FIELD OF THE INVENTION

The invention relates to a surgical forceps. In particular, the invention relates to a surgical cutting stapler.

BACKGROUND OF THE INVENTION

Colon and rectal cancer may be treated laparoscopically by resection. Incidence of local recurrence is one the most important indicators of success postoperatively. Predictors of local recurrence include tumor stage and location of the tumor. However, the surgical resection margins may be considered to be even more important predictors of local recurrence. Important factors correlated with local recurrence include the proximal and distal resection margin (i.e. the upper and lower border of the resection specimen), and the circumferential resection margin (CRM). A positive CRM is correlated with a higher chance of local recurrence.

In distal rectal cancer, the number of resections that still contain tumor tissue at the resection edge has been reported to be up to 30%. Surgeons can encounter problems intra-operatively in finding the optimal distal resection margin, especially in minimally invasive surgery in which tactile feedback is omitted. Ideally the tumor has been marked distally by endoscopically tattooing during the initial endoscopy; visible external tattoos can guide stapler placement and, hence, help in providing adequate distal resection margins. However, this tattoo can be missed due to overlying mesorectal fat in more obese patients (especially in male patients with a narrow pelvis), or if the tattoo has vanished over time after a longer period of neoadjuvant treatment. On the other hand, removing too much healthy tissue distal from the tumor will result in reduced quality of life. Better intra-operative guidance may be able to improve these results significantly.

Surgical staplers are known for use in, for example, laparoscopic surgery to remove tumors. A major application for such surgical staplers is in treatment of tumor of the colon and rectum. Surgical staplers may comprise a forceps. The jaws of the forceps may comprise a linear cutter that can cut the tissue grasped by the forceps along a line. On both sides of the linear cutter, there may be staplers arranged on the forceps jaws, to staple the tissue before cutting. EP 3 103 401 A1 discloses an example of a surgical stapler.

Colon-rectum resection operations are known to remove the tumor tissue. However, the precise placement of the stapler and cutter is very important to ensure that the tumor is securely removed while leaving an as large as possible remaining portion of the colon and rectum in place to guarantee optimal bowel function afterwards.

WO 2017/086789 A1 discloses a method and system for providing visual information about a tumor location in human or animal body. An electromagnetic tumor sensor is provided in or very near to the tumor and tracked to determine its location in space, which is mapped to a tumor model. A surgical tool sensor is provided on a surgical tool, and tracked to determine its location in space, which is mapped to a surgical tool model. The body is scanned to obtain information about an anatomical structure. A reference sensor is provided on the body, and tracked to determine its location in space, which is mapped to the anatomical structure. A virtual image is displayed showing the tumor model, located with the at least one tumor sensor, in spatial relationship to the surgical tool model, located with the at least one surgical tool sensor, and the anatomical structure, located with the at least one reference sensor.

SUMMARY OF THE INVENTION

There is a need for a positioning system for surgical forceps.

In order to address this concern, a surgical forceps is provided comprising
  a forceps comprising a first jaw and a second jaw, the first jaw and the second jaw being configured to be rotated relative to each other around an axis of rotation;
  a position sensor capable of sensing a location, a first orientation with respect to a first axis, and a second orientation with respect to a second axis different from the first axis, wherein the first axis and the second axis are orthogonal to the axis of rotation.

The two orientations provide sufficient information to detect the orientation of the plane in which the forceps jaws can move relative to each other. The distance from this plane to an object can be calculated. This way, it becomes possible to detect with high accuracy where the tissue will be grasped by the forceps if the jaws are moved towards each other. For example, it becomes possible to determine a distance between the cutting plane and another object, such as a tumor. According to the invention, the position sensor does not need to necessarily be able to detect any third orientation with respect to the axis of rotation, because this third orientation does not significantly influence the location of the grasp, in particular the distance of the grasped tissue to another object, such as a tumor. This allows a relatively simple position sensor to be used. The invention allows thus to ensure the grasping of tissue at a suitable distance from a tumor, taking into account for example a tissue margin.

The surgical forceps may comprise a stapler for stapling a tissue grasped by the surgical forceps and a cutter for cutting the tissue grasped by the surgical forceps along a line. This allows to cut a tissue in a highly controlled manner, while stapling the tissue as well. The position sensor allows to determine with high certainty where the tissue is stapled and cut.

The position sensor may be disposed in a plane that is orthogonal to the axis of rotation, the plane comprising at least part of the cutting line. By thus aligning the position sensor with the cutting line, the position detected by the position sensor may be accurately used with a minimum of compensations.

The position sensor may be configured to sense only the first orientation and the second orientation of three possible orientations. The inventors have realized that it may be omitted to measure the orientation with respect to the axis of rotation of the jaws. By suitably fixing the orientation of the position sensor with respect to the forceps, this allows to use a relatively simple position sensor.

The position sensor may be further configured to sense a location of the surgical forceps, thus forming a 5-degrees-of-freedom position sensor. Such a 5-degrees-of-freedom sensor may be particularly cost effective.

The surgical forceps may comprise a clip, wherein the position sensor is fixed to the clip, the clip is removably attachable to the forceps, and the forceps and the clip comprise cooperating means to align the position sensor with the forceps so that the first axis and the second axis are orthogonal to the axis of rotation. This feature allows the position sensor and the forceps to be packaged, sterilized, used, and disposed of or recycled separately. Moreover, it may allow the position sensor to be used on legacy forceps.

At least one of the first jaw and the second jaw may comprise a fixation element to cooperate with a fixation element of the position sensor to fix the position sensor to an end of the at least one of the first jaw and the second jaw, so that the position sensor extends from the at least one of the first jaw and the second jaw in a direction away from the axis of rotation. This feature may allow the position sensor and the forceps to be packaged, sterilized, used, and disposed of or recycled separately. This feature allows to provide a legacy trocar with a position sensor, without needing any extra objects to be attached outside the circumference of the stapler.

The fixation element of the at least one of the first jaw and the second jaw may comprise at least part of a slit corresponding to the cutting line in the at least one of the first jaw and the second jaw, the slit extending at least up to the end of the at least one of the first jaw and the second jaw. This slit provides a convenient feature on which a position sensor may be fit, for example if the fixation element of the position sensor comprises a protruding element that fits fixedly in the slit.

The surgical forceps may comprise a disposable forceps cartridge, such as a stapler cartridge. The disposable forceps cartridge may comprise a space formed to receive and hold the position sensor. This provides a convenient place to use for the position sensor. Moreover, it allows the position sensor to be included in a disposable cartridge, thus allowing the use of legacy forceps.

According to another aspect of the invention, a clip may be provided that is removably attachable to the surgical forceps set forth, the clip comprising a position sensor and a fixation element to cooperate with a fixation element of the surgical forceps to align the position sensor with the surgical forceps so that the roll and the pitch are orthogonal to the axis of rotation of the jaws of the surgical forceps. This provides a particularly flexible arrangement of the position sensor, allowing for many different types of forceps to be provided with a position sensor as an add-on.

According to another aspect of the invention, a position sensor is provided comprising a fixation element to be removably attachable to the surgical forceps set forth, the fixation element of the position sensor being configured to cooperate with a fixation element of at least one of the first jaw and the second jaw of the surgical forceps to fix the position sensor to an end of the at least one of the first jaw and the second jaw, so that the position sensor extends from the at least one of the first jaw and the second jaw in a direction away from the axis of rotation of the jaws, wherein the position sensor is configured to sense at least a first orientation with respect to a first axis and a second orientation with respect to a second axis different from the first axis, wherein the first axis and the second axis are orthogonal to the axis of rotation of the surgical forceps. This provides a particularly favorable manner to provide a forceps with the position sensor as an add-on.

According to another aspect of the invention, a disposable forceps cartridge is provided for being inserted into at least one jaw of the first jaw and the second jaw of the forceps set forth, the disposable stapler cartridge comprising a plurality of staplers on both sides of a cutting line and comprising a space configured to receive and hold a position sensor, wherein the position sensor is configured to sense at least a first orientation with respect to a first axis and a second orientation with respect to a second axis different from the first axis, wherein the first axis and the second axis are orthogonal to the axis of rotation of the surgical forceps. The cartridge provides a way to provide the position sensor as an add-on to existing staplers. Moreover, the inventors found that the staplers known in the art have a portion that is not used for another purpose, so that there is room for including the position sensor in existing stapling cartridges. This way, this provides a particularly convenient solution.

According to another aspect of the invention, a drilling jig is provided comprising a space to receive and hold in a fixed position at least a portion of a disposable stapler cartridge comprising a plurality of staplers, the disposable stapler cartridge for being inserted into at least one jaw of the first jaw and the second jaw of the surgical stapler set forth, the disposable stapler cartridge defining a cutting line and comprising a plurality of staplers, the drilling jig comprising an alignment element to align a drill with respect to the held disposable stapler cartridge to drill a hole in the disposable stapler cartridge at a predetermined position of the disposable stapler cartridge, the hole forming a space configured to receive and hold a position sensor, wherein the position sensor is configured to sense at least a roll and a pitch of the surgical stapler, wherein the roll and the pitch are orthogonal to the axis of rotation of the at least one jaw of the surgical stapler, the drilling jig comprising walls for enclosing the space with at least the stapling mechanism of the disposable stapler cartridge to protect the staplers from particles generated by the drilling, wherein a portion of the cartridge that is to receive the drill extends from the space. This provides a particularly convenient tool to add the position sensor to an existing stapling cartridge.

Regarding the drilling jig, the alignment element may comprise a drilling hole defining a drilling position and a drilling direction with respect to the disposable stapler cartridge. This is a convenient way to guide the drill.

The person skilled in the art will understand that the features described above may be combined in any way deemed useful.

BRIEF DESCRIPTION OF THE DRAWINGS

In the following, aspects of the invention will be elucidated by means of examples, with reference to the drawings. The drawings are diagrammatic and may not be drawn to scale. Throughout the drawings, similar items may be marked with the same reference numerals.

DETAILED DESCRIPTION OF EMBODIMENTS

Figure 1:
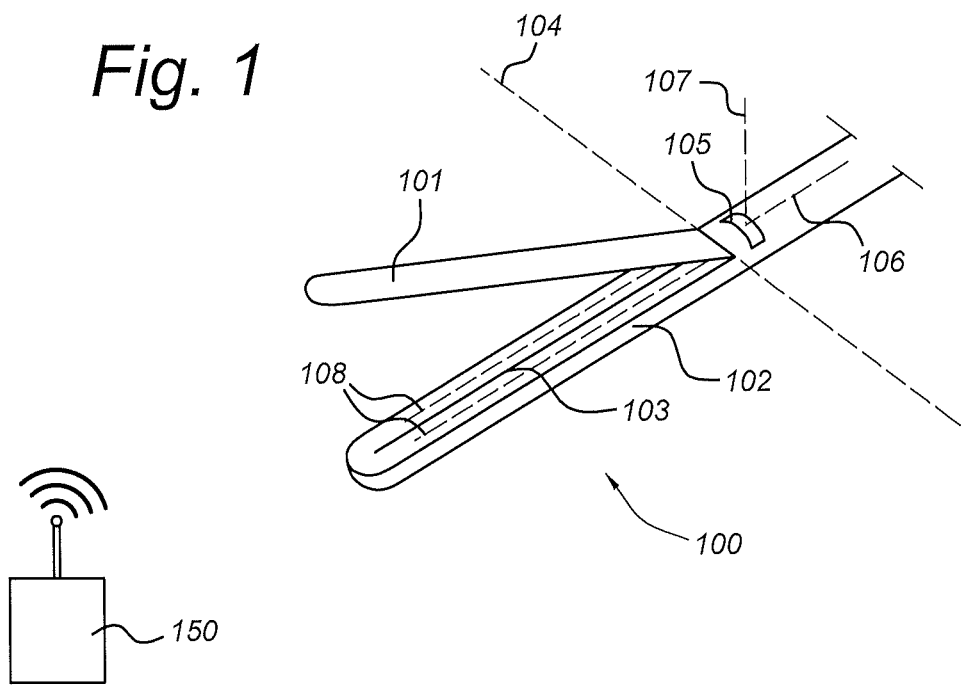
FIG. 1 shows a schematic of a linear cutting stapler.

Certain exemplary embodiments will be described in greater detail, with reference to the accompanying drawings.

The matters disclosed in the description, such as detailed construction and elements, are provided to assist in a comprehensive understanding of the exemplary embodiments. Accordingly, it is apparent that the exemplary embodiments can be carried out without those specifically defined matters. Also, well-known operations or structures are not described in detail, since they would obscure the description with unnecessary detail.

Image-guided navigation surgery allows for full utilization of pre-operative imaging during surgery. It has the potential of increasing the number of radical resections and reducing morbidity caused by damaged surrounding structures or too extensive removal of normal tissue or bowel parts. During surgery, a tracking, e.g. electromagnetic or optical, system may be used to track the patient, tumor and/or surgical instrument(s).

One major challenge is when the tumor is mobile, i.e. the position varies over time due to the location inside the body or due to the surgical procedure. Certain tumor types exhibit mobility because they have less fixed anatomy. For example, in rectal surgery, it is of utmost importance to accurately know the tumor border during surgery for radical resection and minimal damage to or removal of healthy tissue for functional outcome.

This can be achieved by accurately tracking the tumor and a surgical instrument live during surgery. In particular, knowing the exact distance between the tumor and the cutting line of the surgical stapler, will allow the surgeon to optimally place the stapler with respect to the tumor.

One of the ingredients necessary to determine this distance, is to determine the position of the cutting line of the stapler. Using the techniques disclosed herein, it is possible to integrate a single 5 or 6 degrees of freedom sensor in a linear cutting stapler at a specific position and orientation with respect to the cutting line (or cutting edge). This enables an accurate tracking of the entire cutting line (or cutting edge) of the linear stapler. The orthogonal distance between the cutting line (or cutting edge) and any other tracked structure, such as the tumor, can then be continuously calculated. This ensures a correct placement of the stapler before firing the device. Alternatively, the position sensor applied to the stapler or forceps as disclosed in the present disclosure may be used to identify the location of the cutting plane in a preoperative three-dimensional image dataset, for example, instead of, or in addition to, live tracking of a tumor marker.

One way to achieve 3D tracking of the surgical stapler is by integrating a tracking system with the disposable cartridge of the surgical stapler. An example of such a surgical stapler is a linear cutter stapler. Examples herein show how to track such a linear cutter stapler. However, the techniques may be applied to other types of surgical forceps, staplers, and cutters as well.

Generally, in order to completely monitor the position and orientation of a three-dimensional surgical tool with a tracking system, such as an electromagnetic (EM) tracking system, a six degrees of freedom (6DOF) sensor is needed, to measure the position—in x, y and z coordinates—and its orientation—in roll, pitch and yaw parameters—in relation to, for example, the EM field generator. When a 6DOF sensor is firmly affixed to a surgical tool, its position and orientation with respect to the tool can be determined, first by means of certain calibration protocols and subsequently the tools' position and orientation can be determined in relation to the field generator.

In the present disclosure, techniques are disclosed that enable tracking a surgical forceps, for example a surgical linear stapler, with the use of a single five degrees of freedom (5DOF) position sensor.

FIG. 1 displays a schematic of the mouth of a linear stapler 100 in open position. The stapler 100 comprises a forceps with a first, upper jaw 101 and a second, lower jaw 102. The upper jaw 101 can rotate around axis of rotation 104 towards the lower jaw 102 to grasp a tissue. This rotation of the jaw(s) may be performed by an actuator, which is controlled by a handle, which is not shown in the illustration. In the lower jaw, the cutting line 103 and the staples 108 of the linear stapler 100 have been schematically indicated. The linear stapler 100 comprises a cutting mechanism to cut the tissue grasped in between the upper jaw 101 and the lower jaw 102 along the cutting line 103. Such a cutting mechanism is known in the art per se.

By affixing a position sensor 105, which may be a single 5DOF sensor, orthogonal to a plane defined by the center of the upper and lower jaw of the linear stapler in open position, the line along which the linear stapler cuts can be tracked. The position sensor 105 may be a position sensor of the type that cooperates with a transceiver 150. For example, the transceiver 150 transmits an electromagnetic signal to the position sensor 105, and the position sensor 105 transmits an electromagnetic signal in response to the received signal. The transceiver 150 receives the electromagnetic signal from the position sensor 105, and determines two rotations and the position of the position sensor relative to the transceiver 150 by analyzing the received electromagnetic signal.

The position sensor may have an elongated shape, e.g. a cylindrical shape, wherein the position sensor can detect rotation around two axes of rotation 106, 107 that are perpendicular to the longitudinal axis of the position sensor. In such a case, the longitudinal axis of the position sensor may be parallel to the axis of rotation 104 of the jaws 101, 102.

Alternative types of position sensor are also possible, for example based on an accelerometer and/or gyroscope for orientation detection, and/or a global positioning system (GPS) sensor for location detection. For the position detection, other signals than an EM signal are possible as well. For example, location detection using an optical technique may be feasible in some embodiments.

Further, the position and/or orientation, determined by the position sensor 105 and/or the transceiver 150, may be converted into a digital signal. The position information can then be transmitted as a digital signal from the position sensor 105 or the transceiver 150, via a wireless or wired communication link, for example to a control unit or console (not illustrated) that processes the information and/or displays the position of the linear stapler 100, optionally in the context of an anatomical dataset. To this end, the position sensor 105 and/or the transceiver 150 may comprise a digital communications module that supports, for example, Bluetooth, Wi-Fi, 4G, 5G, or any other digital communications standard. For example, the control unit or console displays the plane KLMN, shown in FIG. 2, as determined using the position sensor, in the anatomical context of the patient.

Figure 2:
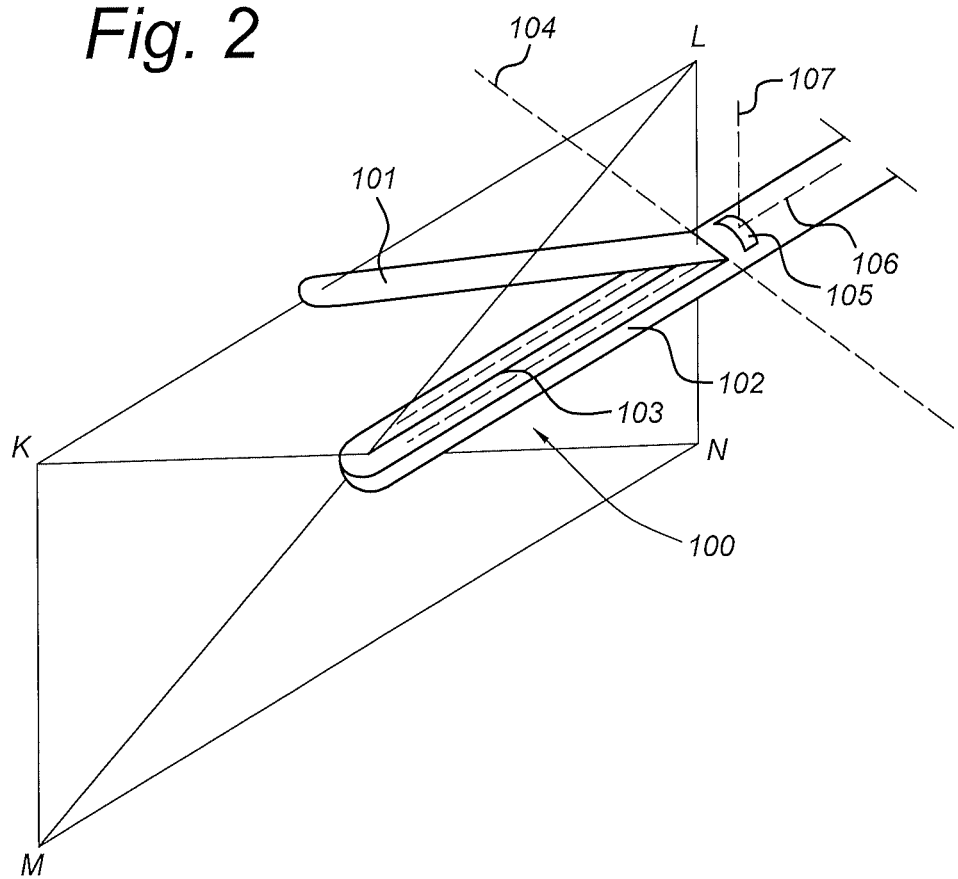
FIG. 2 shows the linear cutting stapler with an indication of a cutting plane.

FIG. 2 illustrates the linear stapler 100 of FIG. 1, in which the aforementioned plane is shown at K, L, M, N. The plane KLMN is a plane intersecting the center of the upper and lower jaw of the stapler, in the open position. Any 5DOF sensor that is placed on this plane and orthogonal to the plane, is able to track the plane. Because this plane defines the cutting line of the linear stapler, it enables tracking of the stapler such that the perioperative placement of the stapler can be aided. Tracking the plane KLMN may be equivalent to tracking a first orientation with respect to a first axis 106 and a second orientation with respect to a second axis 107, wherein the first axis 106 and the second axis 107 are orthogonal to the axis of rotation 104 of the jaws 101, 102. It is noted that the first axis 106 and the second axis 107 are two axes spanning the plane KLMN.

Figure 3A:
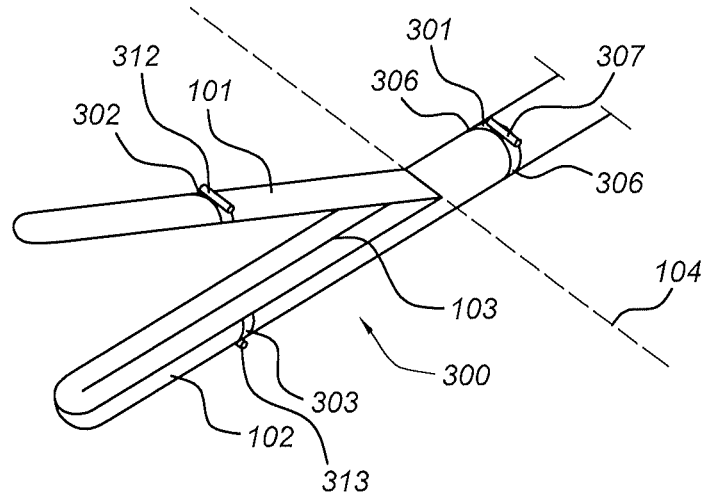
FIG. 3A shows a forceps with a clip.

FIG. 3A illustrates several examples of how the position sensor may be fixed to a forceps 300, which may be a linear stapler, using a clip. In particular, clip 301 is shown with position sensor 307, clip 302 is shown with position sensor 312, and clip 303 is shown with position sensor 313. Although three exemplary positions are illustrated for the clip 301, 302, 303 in the same drawing, it is noted that these are intended to show possible alternative positions. In actual implementations of the present disclosure, it may be sufficient to use only one clip at one selected position. For convenience of illustration only, three possible locations have been indicated in a single figure. Clips can be designed to attach a sensor to the body of the forceps, as shown by means of clip 301, to the upper jaw of the forceps, as shown by means of clip 302, or to the lower jaw of the forceps, as shown by means of clip 303. Note that the sensor of clip 303 is positioned underneath the lower jaw. The arms 306 may be configured to embrace a part of the forceps, such as the body of the forceps, the upper jaw, or the lower jaw. The arms 306 may firmly keep the clip 301 in place. Alternatively, the arms 306 of the clip 301 may form a complete circle around the part of the forceps to which it is attached, for example using a fixation mechanism similar to a tie wrap. Yet alternatively, the clip 301, 302, 303 may be glued to the forceps 300 using an adhesive. In that case, in some embodiments, the arms 306 may be omitted.

Figure 3B:
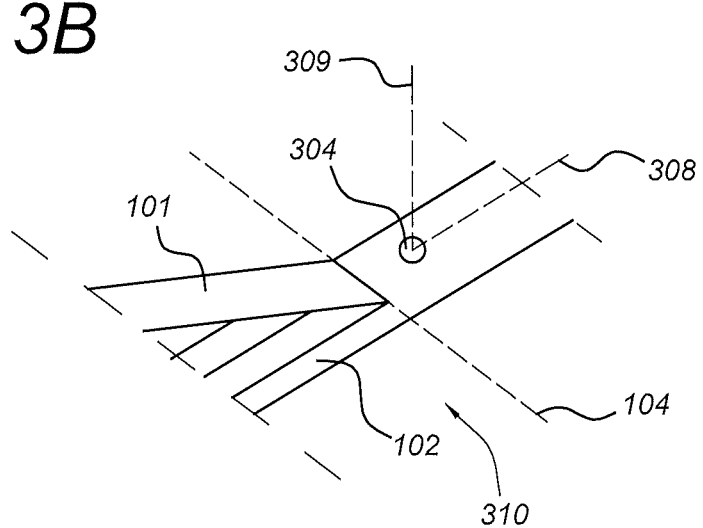
FIG. 3B shows a forceps with a means to align a clip.

FIG. 3B shows a variation of the forceps of FIG. 3A. Shown is an enlargement of a portion of a forceps 310 to which a clip 311 may be attached. The forceps 310 comprises a recess 304 as a means to align the position sensor 307 with the forceps 310 so that the first axis 308 and the second axis 309 are orthogonal to the axis of rotation 104 of the jaws.

Figure 3C:
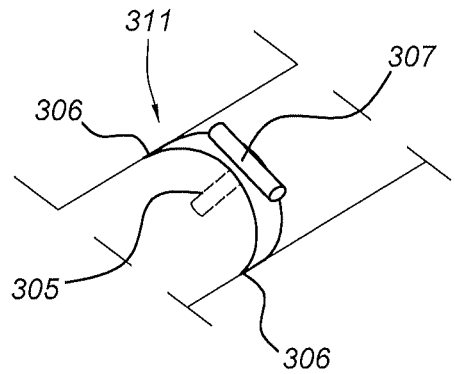
FIG. 3C shows a detail of a forceps with a clip.

FIG. 3C shows the clip 311 to be used with the forceps 310. The clip 311 comprises the position sensor 307, and a protrusion 305 that is configured to engage with the recess 304, as cooperating means to align the position sensor 307 with the forceps 300 so that the first axis 308 and the second axis 309 are orthogonal to the axis of rotation 104. The clip 301 further comprises arms 306 that can embrace the forceps 301 when the protrusion 305 is inserted into the recess 304, so that the clip 301 is fixedly clipped onto the forceps 300.

To keep the orientation of the clip 311 with the position sensor 307 fixed with respect to the forceps 300, the recess 304 and corresponding protrusion 305 may be square or otherwise non-circular in cross section, for example. Alternatively, other fixation means, such as the arms 306 of the clip, can help to prevent rotation of the position sensor 307 with respect to the forceps 300, optionally together with the recess 304, even if the recess 304 and the corresponding protrusion 305 are circular in cross section. As disclosed above with reference to FIG. 3A, the recess 304 and protrusion 305 may be omitted entirely in certain embodiments. Moreover, the examples provided showing how the clip 301, 311 can be fixed to the forceps 300, 310 are not limiting. Other fixation means may be used, and are within the scope of the present disclosure. For example, the clip may be glued to the forceps 300 using an adhesive material.

As discussed above, a possible method to affix the sensor can be with a clip that attaches to the body of the stapler or to the lower jaw of the stapler or to the upper jaw of the stapler. This clip can either be attached to the stapler while the stapler is outside of the body of the patient or while the stapler is inside the body of the patient, after insertion of the stapler, which may be a linear stapler, through a trocar into the human or animal body. These clips are designed in such a way that they do not interfere with the functioning of the linear stapler. The same may apply to other types of surgical forceps.

Figure 4B:
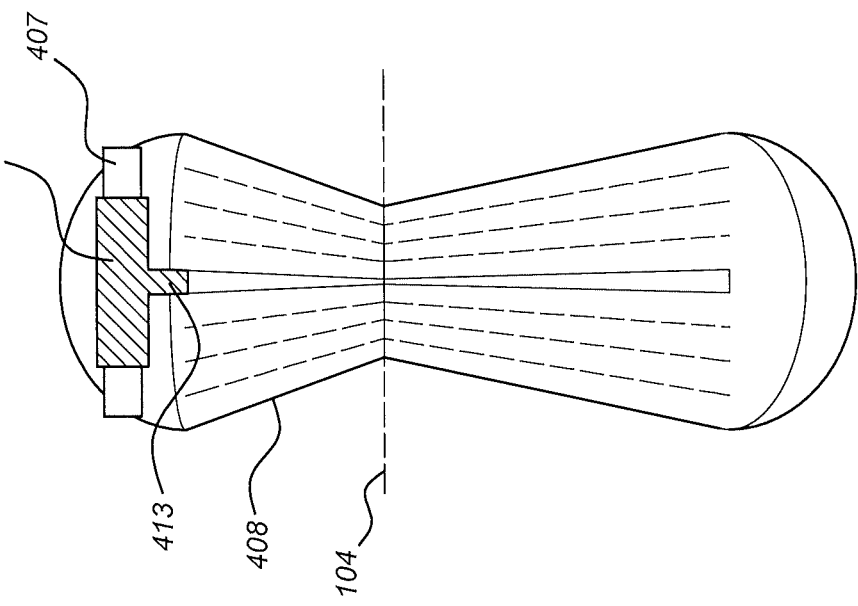
FIG. 4B shows a cutting stapler with a clip clipped into a slit.
Figure 4A:
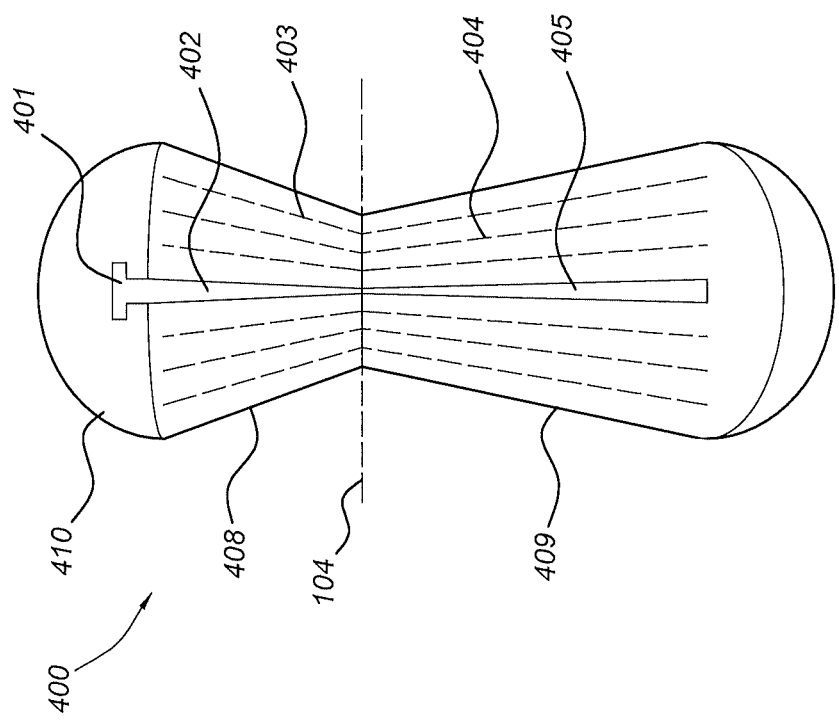
FIG. 4A shows a cutting stapler with a slit extending up to the end of the jaw.

FIGS. 4A and 4B illustrate another example comprising a linear cutter stapler 400 and a clip 406 with a position sensor 407. The clip 406 comprises an insert 413 protruding from the clip 406. The upper jaw 408 of the stapler 400 has a slit 402 corresponding to the cutting line and stapler rows 403 on both sides of the slit 402. FIG. 4A shows a schematic look inside the mouth of the linear stapler 400, pointing out the slit 402 in the upper jaw. The slit 402 extends up to the end 410 of the upper jaw 408. The figure also shows a slit 405 in the lower jaw and stapler rows 404 on both sides of the slit 405. FIG. 4B shows a possible fixation means of a sensor 407 that can be attached into the entrance 401 of the slit 402 at the end of the upper jaw 408 away from the axis of rotation 104, without interfering with the functionality of the linear stapler. The clip 406 has a protruding insert 413 that engages with the entrance 401 of the slit 402 to fix the clip 406 to the stapler 400. This way the clip 406 extends from the upper jaw 408 in a direction away from the axis of rotation 104.

Surgical staplers of the kind discussed in the present disclosure may be designed to be used together with a stapler cartridge. The cartridge may be a disposable component that contains the staples to be stapled into the tissue by the stapler. A cartridge is defined as a disposable stapling and cutting unit that is placed, for example, in the lower jaw of the stapler. A new cartridge may be placed before each time the stapler is fired to insert the staples from the cartridge into the tissue.

Figure 5:
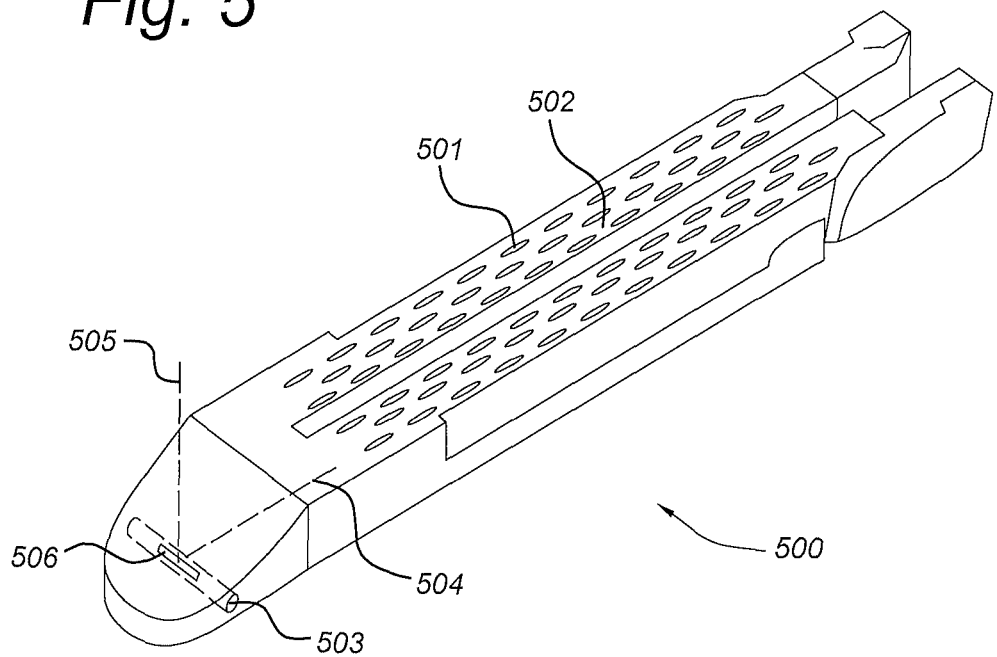
FIG. 5 shows a stapler cartridge.

FIG. 5 shows an example of such a cartridge 500. The cartridge 500 comprises the stapler rows 501 and the cutting slit 502. Moreover, the cartridge 500 comprises a chamber (or hole) 503. The chamber 503 is sized to receive and hold a position sensor 506. In certain embodiments, the position sensor 506 can be inserted into the chamber 503 through an opening in the cartridge giving access to the chamber 503. FIG. 5 shows, by means of example, a detailed schematic of such a cartridge 500 and a potential position of where such a chamber 503 can be placed. This chamber can either be created during the manufacturing process of the cartridge 500 or it can be made afterwards by drilling. This hole 503 can either be drilled before or after sterilization of the cartridge. For example, the hole may be drilled by an end user of the cartridge. In case the hole 503 is drilled during the manufacturing, the position sensor 506 may be provided separately and put into the hole 503 by the end user of the cartridge. Alternatively, the position sensor 506 may be inserted by the manufacturer of the cartridge 500, and the hole 503 may be closed with the position sensor in it.

In certain embodiments, the shape of the position sensor 506 is elongated, so that the position sensor fits in the hole 503, wherein the longitudinal axis of the position sensor is aligned with the central axis of the hole 503, so that the orientation of the position sensor with respect to a first axis 504 and a second axis 505 is predetermined by the shape of the hole 503. Herein, the first axis 504 and the second axis 505 are different from, for example orthogonal to, the longitudinal axis of the position sensor and the central axis of the hole 503. Other ways to fix the orientation of the position sensor with respect to the first axis 504 and the second axis 505 may be considered and are within the scope of the present disclosure. The position sensor may be configured to determine a first orientation around the first axis 504 and a second orientation around the second axis 505. The first axis 504 and second axis 505 may be orthogonal to the axis of rotation 104. In general, when the cartridge 500 is inserted in the stapler 100, this axis of rotation 104 may be orthogonal to the cutting line 502 and parallel to a surface of the area of the stapler cartridge containing the staplers 501.

A potential way to facilitate drilling this hole is to use a drilling jig that ensures that the hole is drilled in the correct position of the cartridge and orthogonal to the plane KLMN.

Figure 6:
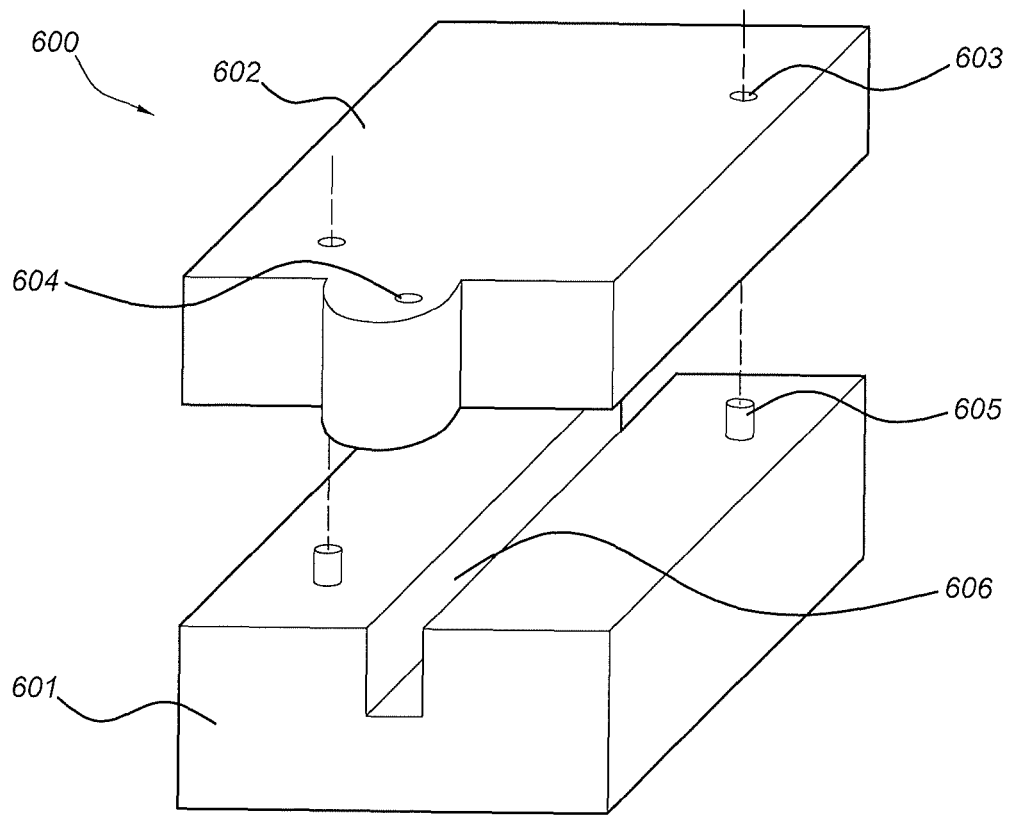
FIG. 6 shows two parts of a drilling jig.

FIG. 6 shows an example of a drilling jig 600 that comprises a first component 601 and a second component 602. The first component 601 comprises alignment holes 603 and a drilling hole 604. The second component 602 comprises alignment pins 605 and a slot 606 to place the stapler cartridge. The drilling jig 600 is designed so that the slot 606 and the second component 602 fully encompass the stapler surfaces 501 of the cartridge 500 in a way to contain the staples within the cartridge and so that any chips that may result from drilling the hole can be vacuumed away, without the risk of the chips ending up in any functional part of the cartridge 500.

Figure 7:
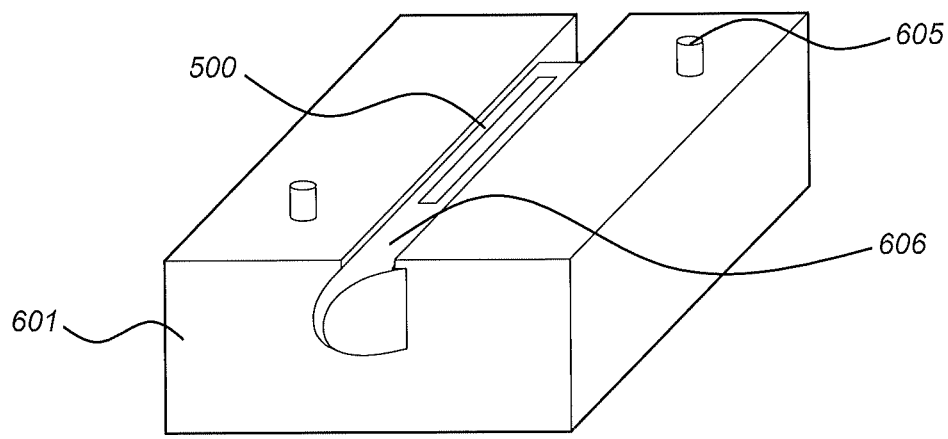
FIG. 7 shows a first part of a drilling jig with a stapler cartridge in it.
Figure 8:
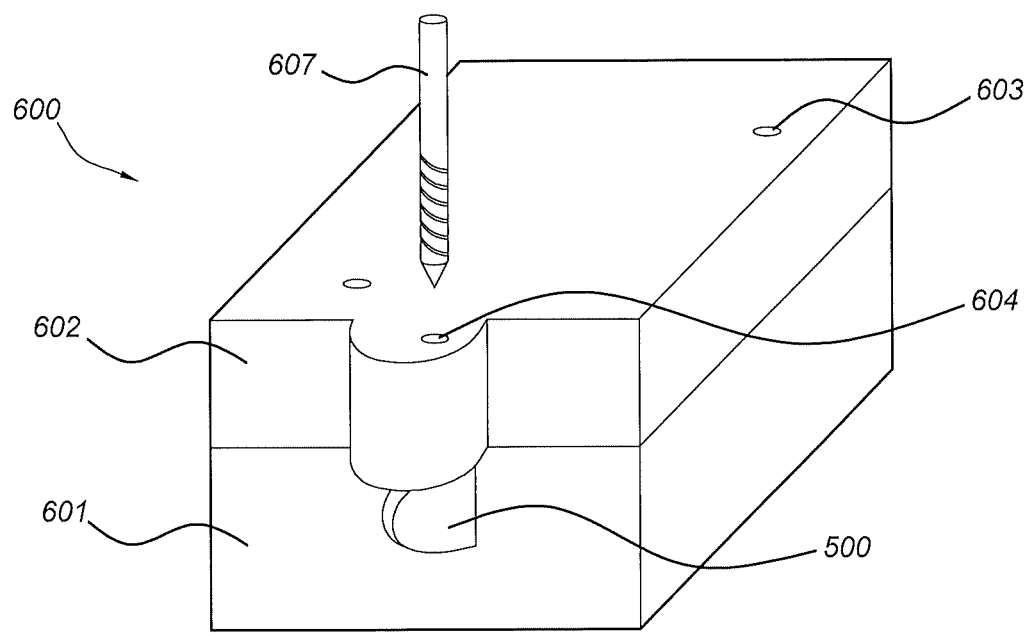
FIG. 8 shows a drilling jig enclosing a part of a stapler cartridge.

FIG. 7 shows the first component 601, with the stapler cartridge 500 placed sideways inside the slot 606. FIG. 8 shows the first component 601, with the stapler cartridge 500 placed sideways inside the slot 606, and the second component 602 put on top of the first component 601 and the stapler cartridge 500, the alignment pins 605 engaging with the alignment holes 603. The drilling hole 604 indicates the position of the hole 503 to be drilled in the stapler cartridge 500 using drill 607.

The hole 503 drilled into the stapler cartridge 500 using the drilling jig 600 forms a space configured to receive and hold the position sensor 506. The position sensor 506 fits in the space such that the orientation of the position sensor 506 is such that the position sensor 506 senses at least a roll and a pitch of the surgical stapler 100, wherein the roll and the pitch are orthogonal to the axis of rotation 104. In general, this axis of rotation 104 is orthogonal to the cutting line 502 and parallel to a surface of the area of the stapler cartridge containing the staplers 501.

Figure 9:
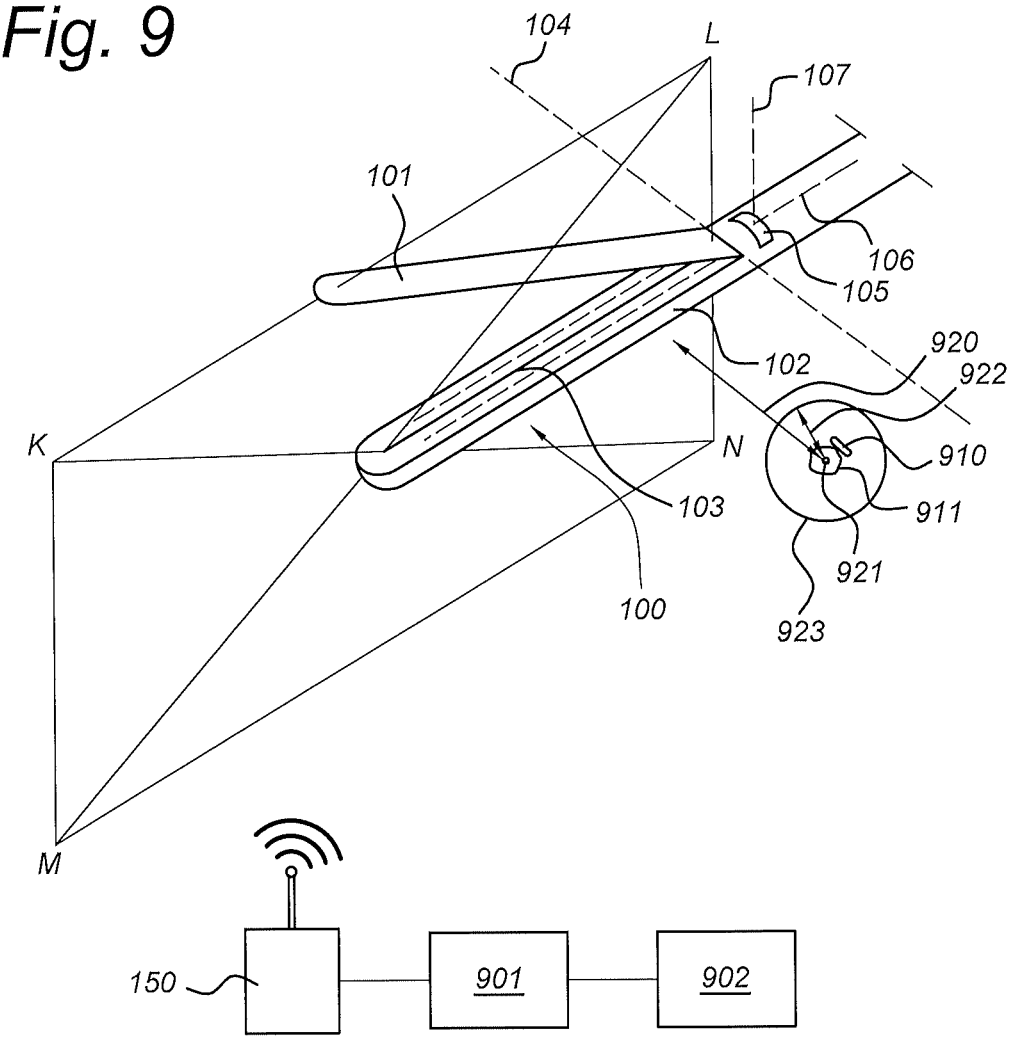
FIG. 9 shows a linear cutting stapler with a processing system.

FIG. 9 shows a position detection system comprising a control unit 901. As illustrated, the system may further comprise a surgical forceps 100, comprising a first jaw 101 and a second jaw 102, the first jaw 101 and the second jaw 102 being configured to be rotated relative to each other around an axis of rotation 104; a position sensor 105 configured to sense a location, a first orientation with respect to a first axis 106, and a second orientation with respect to a second axis 107 different from the first axis 106, wherein the first axis 106 and the second axis 107 are orthogonal to the axis of rotation 104.

The position sensor 105 or the transceiver 150 may be configured to transmit position information, via a wireless or wired communication link, to a control unit 901. The control unit 901 may comprise a computer processor, for example, that is configured to process the position information to determine a position and/or orientation of the stapler 100. In particular, the control unit 901 may be configured to determine the cutting plane, indicated as KLMN in FIG. 9. The surgical forceps 100, including the position sensor 105, and transceiver 150 may be implemented in one of the ways described hereinabove, and will not be described in greater detail hereinafter.

The control unit 901 may be configured to receive further position information from a further position sensor 910. The further position sensor 910 may cooperate with the transceiver 150 in a similar way as the position sensor 105. Alternatively, the further position sensor 910 may be configured to communicate with a different transceiver and/or use a different kind of positioning system. The further position sensor 910 or the transceiver 150 may be configured to transmit further position information, via a wireless or wired communication link, to the control unit 901. The control unit 901 may be configured to determine the position of the further position sensor 910 based on the further position information. The control unit 901 may be optionally further configured to determine the orientation of the further position sensor 910 based on the further position information.

The control unit 901 may be further configured to determine a point of interest 921 based on the position and/or orientation of the further position sensor 910. In the simplest case, the center point of the further position sensor is chosen as the point of interest 921. In that case, no orientation of the further position sensor would be needed.

Alternatively, the control unit 901 may be configured to determine the position of a point of interest 921 at a predetermined position relative to the further position sensor 910. The control unit 901 may be programmed beforehand with the relative position of at least one point of interest 921 with respect to the further position sensor 910, based on e.g. medical image data showing an object 911, such as a tumor, together with the further position sensor 910. For example, the point of interest 921 may correspond to a center of an anatomical object, such as a tumor, or one or more points of interest may correspond to one or more points on a boundary of the anatomical object. The control unit 901 may determine the position of each point of interest 921 based on the position and orientation of the position sensor 910. In certain alternative embodiments, a plurality of further position sensors may be configured to transmit further position information and the control unit 901 may be configured to combine the position information of the plurality of further position sensors to determine the position of the at least one point of interest 921.

The control unit 901 may be further configured to compute a distance 920 from the at least one point of interest 921 to the cutting plane KLMN. This distance may be computed along a line that is perpendicular to the cutting plane KLMN. The control unit 901 may be configured to output an indication of this distance, for example via output unit 902.

The control unit may further be configured to determine a minimal distance 922 from the at least one point of interest 921. For example, the control unit 901 may be programmed with the minimal distance 922. For example, the minimal distance 922 may be a distance from the point of interest 921 to the boundary of a safety margin 923. It is reminded that in certain embodiments, the point of interest may coincide with the further position sensor 910, whereas in certain embodiments, the point of interest may be calculated by the control unit 901 based on the position and/or orientation of the position sensor 910.

The control unit 901 may further be configured to compare the minimal distance 922 to the distance 920 from the point of interest 921 to the cutting plane KLMN, and output a result of the comparison, for example via the output unit 902.

The control unit 901 may be configured to transmit information to output unit 902 configured to output the information. The output unit 902 may comprise at least one of a display screen, a speaker, or a haptic feedback device, for example. For example, the output unit 902 may be configured to display the position of the linear stapler 100 and/or an indication of the cutting plane KLMN, optionally in the context of one or more of the further position sensor 910, the anatomical object 911, the at least one point of interest 921, and/or the minimal distance 922. For example, the control unit 901 and/or output unit 902 may be integrated in a console.

Figure 10:
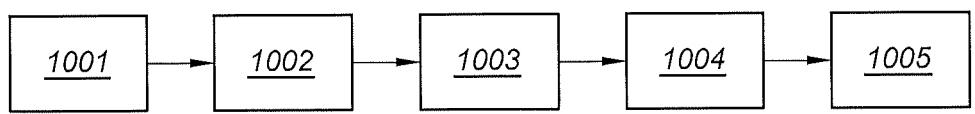
FIG. 10 shows a flowchart illustrating aspects of a method of position detection.

FIG. 10 shows a method, which may be executed for example by the control unit 901.

In step 1001, the control unit 901 receives position information indicative of a location of a position sensor 105 fixed to a stapler 100 and determines a cutting plane KLMN based on the position information.

In step 1002, the control unit 901 receives further position information generated using a further position sensor 910. This further position sensor 910 is separate of the stapler 100.

In step 1003, the control unit 901 determines a location of a point of interest 921 based on the further position information relating to the further position sensor 910. For example, the control unit 901 determines a location and optionally an orientation of the further position sensor 910 based on the further position information, and calculates the location of the point of interest based on the location and/or orientation of the further position sensor 910, and a relative position of the point of interest with respect to the further position sensor. Alternatively, the control unit 901 may set the point of interest equal to the location of the position sensor. Yet alternatively, the control unit 901 may combine further position information from a plurality of the further position sensors to calculate a location of the point of interest.

In step 1004, the control unit 901 calculates a distance 920 from the cutting plane KLMN to the point of interest 921. This distance 920 is measured along a line that is perpendicular to the cutting plane KLMN.

In step 1005, the control unit 901 outputs an indication of the distance 920. For example, the control unit 901 may output the distance 920 itself or an indication of the distance 920 compared to a threshold distance 922.

The distance 920 of the cutting plane KLMN to the point of interest 921 or position sensor 910 may provide important or sufficient information to realize accurate cutting, taking into account e.g. a safety margin around an object to be resected. The distance 920 may be determined using a single 5-degrees-of-freedom position sensor 105 on the surgical forceps 100, although other types of position sensors may be used alternatively. This way, even with a 5-degrees-of-freedom position sensor 105 on the surgical forceps 100, the distance 920 from the cutting plane to the point of interest 921 may be determined. The point of interest 921 may be, for example, any point on the boundary of a tumor. Alternatively, a 6-degrees-of-freedom position sensor may be used to implement the position sensor 105.

Some aspects of the invention, such as the method to be executed by the control unit, may be suitable for being implemented in form of software, in particular a computer program product. The computer program product may comprise a computer program stored on a non-transitory computer-readable media. Also, the computer program may be represented by a signal, such as an optic signal or an electro-magnetic signal, carried by a transmission medium such as an optic fiber cable or the air. The computer program may partly or entirely have the form of source code, object code, or pseudo code, suitable for being executed by a computer system. For example, the code may be executable by one or more processors.

The examples and embodiments described herein serve to illustrate rather than limit the invention. The person skilled in the art will be able to design alternative embodiments without departing from the spirit and scope of the present disclosure, as defined by the appended claims and their equivalents. Reference signs placed in parentheses in the claims shall not be interpreted to limit the scope of the claims. Items described as separate entities in the claims or the description may be implemented as a single item combining the features of the items described.

Certain subject-matter is disclosed in the following clauses.

Clause 1. A surgical forceps, comprising
a first jaw (101) and a second jaw (102), the first jaw (101) and the second jaw (102) being configured to be rotated relative to each other around an axis of rotation (104);
a position sensor (105) configured to sense a location, a first orientation with respect to a first axis (106), and a second orientation with respect to a second axis (107) different from the first axis (106), wherein the first axis (106) and the second axis (107) are orthogonal to the axis of rotation (104).

Clause 2. The surgical forceps of clause 1, wherein the surgical forceps comprises a stapler (108) for stapling a tissue grasped by the surgical forceps (100) and a cutter (103) for cutting the tissue grasped by the surgical forceps (100) along a line.

Clause 3. The surgical forceps of clause 2, wherein the position sensor (105) is disposed in a plane (KLMN) that is orthogonal to the axis of rotation (104), the plane (KLMN) comprising at least part of the cutting line (103).

Clause 4. The surgical forceps of clause 1, wherein the position sensor (105) is configured to sense only the first orientation and the second orientation of three possible orientations.

Clause 5. The surgical forceps of clause 4, wherein the position sensor (105) is a 5-degrees-of-freedom position sensor.

Clause 6. The surgical forceps of clause 1, further comprising a clip (301), wherein:
the position sensor (307) is fixed to the clip (301);
the clip (301) is removably attachable to the forceps (300), and
the forceps (300) and the clip (301) comprise cooperating means (304, 305) to align the position sensor (307) with the forceps (300) so that the first axis (308) and the second axis (309) are orthogonal to the axis of rotation (104).

Clause 7. The surgical forceps of clause 6, wherein at least one of the first jaw (408) and the second jaw (409) comprises a fixation element (401) to cooperate with a fixation element (408) of the clip (406) to fix the position sensor (407) to an end (410) of the at least one of the first jaw (408) and the second jaw (409), so that the clip (406) extends from the at least one of the first jaw (408) and the second jaw (409) in a direction away from the axis of rotation (104).

Clause 8. The surgical forceps of clause 7, wherein the fixation element (401) of the at least one of the first jaw (408) and the second jaw (409) comprises at least part of a slit (402) corresponding to the cutting line (103) in the at least one of the first jaw (408) and the second jaw (409), the slit (402) extending at least up to the end (410) of the at least one of the first jaw (408) and the second jaw (409).

Clause 9. The surgical forceps of clause 1, further comprising a disposable forceps cartridge, such as a stapler cartridge (500), comprising a space (503) formed to receive and hold the position sensor (105).

Clause 10. A clip that is removably attachable to the surgical forceps of any one of clauses 1 to 9, the clip (301) comprising a position sensor (307) and a fixation element (305) to cooperate with a fixation element (304) of the surgical forceps (300) to align the position sensor (307) with the surgical forceps (300) so that the first axis (308) and the second axis (309) are orthogonal to the axis of rotation (104) of the jaws (101, 102) of the surgical forceps (300).

Clause 11. The clip of clause 10, wherein the fixation element (408) is configured to cooperate with a fixation element (401) of at least one of the first jaw (408) and the second jaw (409) of the surgical forceps (400) to fix the position sensor (407) to an end (410) of the at least one of the first jaw (408) and the second jaw (409), so that the clip (406) extends from the at least one of the first jaw (408) and the second jaw (409) in a direction away from the axis of rotation (140), wherein the position sensor (407) is configured to sense at least a first orientation with respect to a first axis and a second orientation with respect to a second axis different from the first axis, wherein the first axis and the second axis are orthogonal to the axis of rotation (104) of the surgical forceps.

Clause 12. A stapler cartridge for being inserted into at least one jaw of the first jaw (101) and the second jaw (102) of the surgical forceps (100) of any one of clauses 1 to 9, the stapler cartridge (500) comprising a plurality of staplers (501) on both sides of a cutting line (502) and comprising a space (503) configured to receive and hold a position sensor, wherein the space (503) is shaped so that, when the position sensor is in place in the space (503) and the stapler cartridge is in its position in said at least one jaw of the surgical forceps, the position sensor is configured to sense at least a first orientation with respect to a first axis (504) and a second orientation with respect to a second axis (505) different from the first axis (504), wherein the first axis (504) and the second axis (505) are orthogonal to an axis of rotation (104), wherein the axis of rotation (104) is orthogonal to the cutting line (502) and the axis of rotation (104) is orthogonal to a shooting direction of the staplers (501).

Clause 13. The stapler cartridge of clause 12, further comprising the position sensor fixed inside the stapler cartridge, wherein the position sensor is configured to sense at least the first orientation with respect to the first axis (504) and the second orientation with respect to the second axis (505) different from the first axis (504).

Clause 14. A drilling jig comprising a space (606) to receive and hold in a fixed position at least a portion of a stapler cartridge (500) comprising a plurality of staplers (501), the stapler cartridge (500) for being inserted into at least one jaw (102) of the first jaw and the second jaw of the surgical forceps of any one of clauses 1 to 9, the stapler cartridge (500) defining a cutting line (103) and comprising a plurality of staplers (108), the drilling jig comprising an alignment element (604) to align a drill (607) with respect to the held stapler cartridge (606) to drill a hole (503) in the stapler cartridge (500) at a predetermined position of the stapler cartridge (500), the hole forming a space configured to receive and hold a position sensor in a position to sense at least a roll and a pitch of the surgical stapler, wherein the roll and the pitch are orthogonal to the axis of rotation of the at least one jaw of the surgical stapler, the drilling jig (600) comprising walls for enclosing the space (606) with at least the staples (501) of the stapler cartridge to protect the staples (501) from particles generated by the drilling, wherein a portion of the cartridge (500) that is to receive the drill extends from the space (606).

Clause 15. The drilling jig of clause 14, wherein the alignment element (604) comprises a drilling hole defining a drilling position and a drilling direction with respect to the stapler cartridge.

The invention claimed is:

1. A system for processing position information, the system comprising
a control unit configured to:
receive position information indicative of a location, a first orientation with respect to a first axis, and a second orientation with respect to a second axis different from the first axis, wherein the first axis and the second axis are orthogonal to an axis of rotation of a first jaw and a second jaw of a surgical forceps, the first jaw and the second jaw being configured to be rotated relative to each other around the axis of rotation, and determine a cutting plane of the surgical forceps based on the position information;
receive further position information associated with at least one first position sensor;
determine a location of a point of interest based on the further position information; and
calculate a distance from the cutting plane to the point of interest, wherein the distance is measured perpendicular to the cutting plane.

2. The system of claim 1, wherein the control unit is configured to determine a location of the at least one first position sensor based on the further position information and determine the location of the point of interest based on the location of the at least one first position sensor.

3. The system of claim 1, further comprising the surgical forceps comprising the first jaw and the second jaw, the first jaw and the second jaw being configured to be rotated relative to each other around the axis of rotation, the surgical forceps further comprising a second position sensor configured to sense the location, the first orientation with respect to the first axis, and the second orientation with respect to the second axis different from the first axis, wherein the first axis and the second axis are orthogonal to the axis of rotation.

4. The system of claim 3, further comprising the at least one first position sensor.

5. The system of claim 3, further comprising a disposable forceps cartridge, such as a stapler cartridge, comprising a space formed to receive and hold the second position sensor.

6. The system of claim 5, wherein the surgical forceps comprises a stapler for stapling a tissue grasped by the surgical forceps and a cutter for cutting the tissue grasped by the surgical forceps along a line.

7. The system of claim 6, wherein the second position sensor is disposed in a plane that is orthogonal to the axis of rotation, the plane comprising at least part of the cutting line.

8. The system of claim 3, further comprising a clip, wherein:
the second position sensor is fixed to the clip;
the clip is removably attachable to the forceps, and
the forceps and the clip comprise cooperating means to align the second position sensor with the forceps so that the first axis and the second axis are orthogonal to the axis of rotation.

9. The system of claim 8, wherein at least one of the first jaw and the second jaw comprises a fixation element to cooperate with a fixation element of the clip to fix the position sensor to an end of the at least one of the first jaw and the second jaw, so that the clip extends from the at least one of the first jaw and the second jaw in a direction away from the axis of rotation.

10. The system of claim 9, wherein the fixation element of the at least one of the first jaw and the second jaw comprises at least part of a slit corresponding to the cutting line in the at least one of the first jaw and the second jaw, the slit extending at least up to the end of the at least one of the first jaw and the second jaw.

11. The system of claim 1, wherein the second position sensor is configured to sense only the first orientation and the second orientation of three possible orientations, and/or wherein the second position sensor is a 5-degrees-of-freedom position sensor.

12. The system of claim 1, further comprising a stapler cartridge for being inserted into at least one jaw of the first jaw and the second jaw of the surgical forceps, the stapler cartridge comprising a plurality of staplers on both sides of a cutting line and comprising a space configured to receive and hold a second position sensor, wherein the space is shaped so that, when the second position sensor is in place in the space and the stapler cartridge is in its position in said at least one jaw of the surgical forceps, the second position sensor is configured to sense at least the first orientation with respect to the first axis and the second orientation with respect to the second axis different from the first axis, wherein the first axis and the second axis are orthogonal to the axis of rotation, wherein the axis of rotation is orthogonal to the cutting line and the axis of rotation is orthogonal to a shooting direction of the staplers.

13. A computer-implemented method for processing position information, the method comprising
receiving, by a control unit, position information indicative of a location, a first orientation with respect to a first axis, and a second orientation with respect to a second axis different from the first axis, wherein the first axis and the second axis are orthogonal to an axis of rotation of a first jaw and a second jaw of a surgical forceps, the first jaw and the second jaw being configured to be rotated relative to each other around the axis of rotation, and determine a cutting plane of the surgical forceps based on the position information;
receiving, by the control unit, further position information associated with at least one first position sensor;
determining, by the control unit, a location of a point of interest based on the further position information; and
calculating, by the control unit, a distance from the cutting plane to the point of interest, wherein the distance is measured perpendicular to the cutting plane.

* * * * *